United States Patent [19]

Page et al.

[11] Patent Number: 4,870,038

[45] Date of Patent: Sep. 26, 1989

[54] OLEFIN OLIGOMERIZATION WITH SURFACE MODIFIED ZEOLITE CATALYST

[75] Inventors: Nancy M. Page, Yardley, Pa.; Lewis B. Young, Skillman, N.J.; David A. Blain, Yardley, Pa.

[73] Assignee: Mobil Oil Corporation, New York, N.Y.

[21] Appl. No.: 140,361

[22] Filed: Jan. 4, 1988

Related U.S. Application Data

[63] Continuation-in-part of Ser. No. 105,438, Oct. 7, 1987, abandoned.

[51] Int. Cl.$^4$ ............................................. B01J 29/06
[52] U.S. Cl. ...................................................... 502/62
[58] Field of Search ......................................... 502/62

[56] References Cited

U.S. PATENT DOCUMENTS

| | | | |
|---|---|---|---|
| 2,143,566 | 1/1939 | Moser | 196/10 |
| 2,318,719 | 5/1943 | Schneider et al. | 196/10 |
| 4,029,719 | 4/1977 | Forni et al. | 260/683 |
| 4,104,151 | 8/1978 | Rubin et al. | 208/111 |
| 4,298,547 | 11/1981 | Young et al. | 260/505 |
| 4,300,011 | 11/1981 | Rollmann | 585/467 |
| 4,359,595 | 11/1982 | Rollmann | 585/640 |
| 4,469,912 | 9/1984 | Blewett et al. | 585/525 |
| 4,520,221 | 5/1985 | Chen | 585/517 |
| 4,568,786 | 2/1986 | Chen et al. | 585/517 |
| 4,658,079 | 4/1987 | Chen | 585/517 |
| 4,663,140 | 5/1987 | Van Erp et al. | 502/62 |
| 4,675,460 | 6/1987 | Seddon et al. | 585/329 |

FOREIGN PATENT DOCUMENTS

| | | |
|---|---|---|
| 1205792 | of 0000 | Canada . |
| 474885 | 11/1937 | United Kingdom . |
| 479657 | 2/1938 | United Kingdom . |

*Primary Examiner*—Patrick P. Garvin
*Assistant Examiner*—George R. Fourson
*Attorney, Agent, or Firm*—A. J. McKillop; C. J. Speciale; E. F. Kenehan, Jr.

[57] ABSTRACT

A process for producing substantially linear hydrocarbons by oligomerizing a lower olefin at elevated temperature and pressure which comprises contacting the lower olefin under oligomerization/polymerization conditions with siliceous acidic ZSM-23 zeolite having Brönsted acid activity; wherein the zeolite has acidic pore activity and wherein the zeolite surface is rendered substantially inactive for acidic reactions. The zeolite surface can be neutralized by a bulky pyridine compound having an effective cross-section larger than the zeolite pore. The preferred deactivating agent is 2,4,6-collidine, which may be applied to the zeolite as a pretreatment or added with olefin feed in a continuous process. The olefin oligomers may be used as alkylating agents to prepare biodegradable alkylbenzenes and alkylphenylsulfonates. A preferred catalyst for this alkylation reaction is dealuminized mordenite.

4 Claims, No Drawings

OLEFIN OLIGOMERIZATION WITH SURFACE MODIFIED ZEOLITE CATALYST

CROSS-REFERENCE TO RELATED APPLICATIONS

This application is a continuation-in-part of copending U.S. Application Ser. No. 105,438, filed Oct. 7, 1987, now abandoned, the entire disclosure of which is expressly incorporated herein by reference. This application is also related to copending U.S. Application Ser. No. 105,434, filed Oct. 7, 1987, now abandoned, the entire disclosure of which is also expressly incorporated herein by reference.

BACKGROUND

This application discloses a process for producing high molecular weight hydrocarbons from a lower olefin feedstock by employing a shape selective crystalline silicate catalyst which is surface inactivated.

Recent work in the field of olefin upgrading has resulted in a catalytic process for converting lower olefins to heavier hydrocarbons. Heavy distillate and lubricant range hydrocarbons can be synthesized over ZSM-5 type catalysts at elevated temperature and pressure to provide a product having substantially linear molecular conformations due to the ellipsoidal shape selectivity of certain medium pore catalysts.

Conversion of olefins to gasoline and/or distillate products is disclosed in U.S. Pat. Nos. 3,960,978 and 4,021,502 (Givens, Plank and Rosinski) wherein gaseous olefins in the range of ethylene to pentene, either alone or in admixture with paraffins are converted into an olefinic gasoline blending stock by contacting the olefins with a catalyst bed made up of a ZSM-5 type zeolite. Such a technique has been developed by Garwood, et al, disclosed in European Patent Application No. 83301391.5, published Sept. 29, 1983. U.S. Pat. Nos. 4,150,062; 4,211,640; 4,227,992; and 4,547,613 Garwood, et al disclose operating conditions for a process for selective conversion of $C_3+$ olefins to mainly aliphatic hydrocarbons.

In the process for catalytic conversion of olefins to heavier hydrocarbons by catalytic oligomerization using a medium pore shape selective acid crystalline zeolite, process conditions can be varied to favor the formation of hydrocarbons of varying molecular weight. At moderate temperature and relatively high pressure, the conversion conditions favor $C_{10}+$ aliphatic product. Lower olefinic feedstocks containing $C_2-C_8$ alkenes may be converted; however, the distillate mode conditions do not convert a major fraction of ethylene. A typical reactive feedstock consists essentially of $C_3-C_6$ mono-olefins, with varying amounts of non-reactive paraffins and the like being acceptable components.

It is known to use certain basic materials to deactivate the Brösted acid sites on the surface of aluminosilicate catalysts. U.S. Pat. No. 4,520,211 and U.S. Pat. No. 4,568,786, Chen, et al., which are expressly incorporated herein disclose bulky amines, such as di-tert-butyl pyridine, as such basic materials.

Shape-selective oligomerization, as it applies to the conversion of $C_2-C_{10}$ olefins over ZSM-5, may produce higher olefins up to $C_{30}$ and higher. As reported by Garwood in "Intrazeolite Chemistry 23", (Amer. Chem. Soc., 1983), reaction conditions favoring higher molecular weight product are low temperature (200°–260° C.), elevated pressure (about 2000 kPa or greater), and long contact time (less than 1 WHSV). The reaction under these conditions proceeds through the acid-catalyzed steps of (1) oligomerization, (2) isomerization-cracking to a mixture of intermediate carbon number olefins, and (3) interpolymerization to give a continuous boiling product containing all carbon numbers. The channel systems of medium pore catalysts impose shape-selective constraints on the configuration of the large molecules, accounting for the difference with other catalysts.

The desired oligomerization-polymerization products include $C_{10}+$ substantially linear aliphatic hydrocarbons. This catalytic path for propylene feed provides a long chain which generally has lower alkyl (e.g., methyl) substituents along the straight chain.

The final molecular configuration is influenced by the pore structure of the catalyst. For the higher carbon numbers, the structure is primarily a methyl-branched straight olefinic chain, with the maximum cross-section of the chain limited by the dimension of the largest zeolite pore. Although emphasis is placed on the normal 1-alkenes as feedstocks, other lower olefins, such as 2-butene or isobutylene, are readily employed as starting materials due to rapid isomerization over the acidic zeolite catalysts. At conditions chosen to maximize heavy distillate and lubricant range products ($C_{20}+$), the raw aliphatic product is essentially mono-olefinic. Overall branching is not extensive and may occur at spaced positions within the molecule.

The viscosity index of a hydrocarbon lube oil is related to its molecular configuration. Extensive branching in a molecule usually results in a low viscosity index. It is believed that two modes of oligomerization/polymerization of olefins can take place over acidic zeolites, such as HZSM-5. One reaction sequence takes place at Brösted acid sites inside the channels or pores, producing essentially linear materials. The other reaction sequence occurs on the outer surface, producing more branched material. By decreasing the surface acid activity of such zeolites, fewer highly branched products with low VI are obtained.

Several techniques may be used to increase the relative ratio of intra-crystalline acid sites to surface active sites. This ratio tends to increase with crystal size due to geometric relationship between volume and superficial surface area. Deposition of carbonaceous materials by coke formation can also shift the effective ratio, as disclosed in U.S. Pat. No. 4,547,613.

The Young U.S. Pat. Nos. 4,301,316; 4,301,317; and 4,298,547, the entire disclosures of which are expressly incorporated by reference, disclose methods for using linear olefins, whereby these olefins are reacted with benzene in a particular way and then sulfonated to form biodegradable alkylbenzene sulfonic acid based detergents, particularly 2-phenylalkane sulfonates.

SUMMARY

According to one aspect of this application, there is provided a process for producing substantially linear hydrocarbons by oligomerizing a lower olefin at elevated temperature and pressure which comprises contacting the lower olefin under polymerization conditions with siliceous acidic ZSM-23 zeolite having Brösted acid activity; wherein said zeolite has acidic pore activity and wherein the zeolite surface is rendered substantially inactive for acidic reactions, said zeolite surface being neutralized by a bulky trialkyl pyridine compound having an effective cross-section larger than the zeolite pore.

According to another aspect of this application, there is provided a process for producing heavier hydrocarbons by oligomerizing lower olefin feed at elevated temperature and pressure which comprises contacting the lower olefin under oligomerization conditions with a medium pore shape-selective siliceous zeolite catalyst having acid cracking activity, and a constraint index of about 8 to 10, wherein said zeolite has internal acidic pore activity and wherein the zeolite surface is rendered substantially inactive for acidic reactions by chemisorption of a 2,4,6-trialkyl pyridine deactivating agent, having $C_2$ to $C_4$ alkyl groups.

According to another aspect of this application, there is provided a surface-inactivated catalyst composition comprising acid crystalline ZSM-23 having active internal Brösted acid sites and containing a surface-inactivating amount of 2,4,6-collidine.

According to another aspect of this application, there is provided a method of making a shape-selective catalyst comprising contacting acid medium pore ZSM-23 zeolite with a solution of a bulky trialkyl pyridine deactivating agent to chemisorb said agent onto the zeolite surface for rendering said zoelite surface substantially inactive for acidic reaction.

According to another aspect of this invention, there is provided a process for producing substantially linear hydrocarbons by oligomerizing a lower olefin at elevated temperature and pressure which comprises contacting the lower olefin under polymerization conditions with siliceous acidic ZSM-23 zeolite having Brösted acid activity; wherein said zeolite has acidic pore activity and wherein the zeolite surface is rendered substantially inactive for acidic reactions, said zeolite surface being neutralized by a bulky pyridine compound having an effective cross-section larger than the zeolite pore.

According to another aspect of this application there is provided a multi-stage process for producing high viscosity index lubricating oils from lower olefin feed which comprises contacting the lower olefins in a primary reaction zone under conditions of elevated temperature and pressure with a medium pore shape-selective siliceous zeolite catalyst having Bronsted acid activity, and a constraint index of about 1 to 12; wherein said zeolite has acidic pore activity and wherein the zeolite surface is rendered substantially inactive for acidic reactions, said zeolite surface being neutralized by a bulky trialkyl pyridine deactivating agent having an effective cross-section larger than the zeolite pore to produce substantially linear $C_{10}^+$ intermediate olefins; and contacting at least a portion of the primary stage effluent in a secondary reaction zone with an acid catalyst to effectively polymerize the $C_{10}^+$ hydrocarbons.

According to other aspects of this application, there are provided oligomers which may be produced by processes described herein.

According to other aspects of this application, there are provided processes for preparing certain organic compounds from mono-olefins, particularly olefin oligomers, described herein. One such process involves the selective alkylation of an aromatic compound with a relatively long chain length alkylating agent to produce substantially linear phenylalkanes enriched in the 2-phenylalkane isomer; said alkylating agent comprising mono-olefins having at least 9 carbon atoms as described herein;

said process comprising contacting said aromatic compound with said alkylating agent in the presence of a selective zeolite catalyst under sufficient conditions, said selective zeolite catalyst being characterized by a crystal structure having channels or network of pores therethru, the major dimension of the openings to said channels or networks of pores being between about 6 and about 7 angstroms.

This phenylalkane can, in turn, be converted to an alkylbenzene sulfonate by a process comprising sulfonating the phenylalkane.

EMBODIMENTS

It has been discovered that when a surface-inactivated, but internally active, ZSM-23 metallosilicate zeolite catalyst is employed in olefin oligomerization, the reaction yields a high quality, essentially linear oligomer stock which can be efficiently converted to high VI lube oils. The catalyst can be surface inactivated in situ by cofeeding a sterically hindered basic amine compound with the olefinic feedstock, or the novel catalyst can be treated in a separate step prior to olefin oligomerization.

Unless otherwise specified, metric units and parts-by-weight (pbw) are utilized in the description and examples.

Recent developments in zeolite technology have provided a group of medium pore siliceous materials having similar pore geometry. Prominent among these intermediate pore size zeolites is ZSM-23, which may be synthesized with Brösted acid active sites by incorporating a tetrahedrally coordinated metal, such as Al, Ga, or Fe, within the zeolitic framework. These medium pore zeolites are favored for acid catalysis; however, the advantages of ZSM-23 structures may be utilized by employing highly siliceous materials or crystalline metallosilicate having one or more tetrahedral species having varying degrees of acidity. ZSM-23 crystalline structure is readily recognized by its X-ray diffraction pattern, which is described in U.S. Pat. No. 4,076,842 (Rubin, et al.), incorporated by reference.

The shape-selective oligomerization/polymerization catalysts preferred for use herein include the crystalline aluminosilicate zeolites having a silica-to-alumina molar ratio of at least 12, a constraint index of about 8 to 10, and acid cracking activity (alpha value) of about 10–300. A suitable shape selective medium pore catalyst for fixed bed is a small crystal H-ZSM-23 zeolite having alpha value of about 25, with alumina binder in the form of cylindrical extrudates of about 1–5 mm. The preferred catalyst consists essentially of ZSM-23 having a crystallite size of about 0.02 to 2 microns, with framework metal synthesized as gallo-silicate, ferrosilicate, and/or aluminosilicate. These zeolites have a pore size of $4.5 \times 5.6$ Angstroms, such as to freely sorb normal hexane. In addition, the structure must provide constrained access to larger molecules.

It is generally understood that the proportion of internal acid sites relative to external acid sites increases with larger crystal size. However, the smaller crystallites, usually less than 0.1 micron, are preferred for diffusion-controlled reactions, such as oligomerization, polymerization, etc. Accordingly, it may be required to neutralize more than 15% of the total Brösted acid sites by chemisorption of the basic deactivating agent.

The degree of steric hindrance should also be considered in the choice of the basic nitrogen compounds, especially the bulky trialkyl pyridine species having alkyl groups of 1 to 4 carbon atoms. Although the selected organonitrogen compound must be bulky enough to prevent infusion of said compound into the internal pores of the catalyst, excessive steric hindrance may prevent effective or complete interaction between the surface Brösted acid site and the selected basic species.

Catalysts of low surface activity can be obtained by using medium pore, shape selective ZSM-23 zeolites of small crystal size that have been deactivated by one or more trialkyl pyridine compounds, such as 2,4,6-collidine (2,4,6-trimethyl pyridine, gamma-collidine). These compounds all must have a minimum cross-section diameter greater than the effective pore size of the zeolite to be treated; i.e., greater than 5 Angstroms.

When propylene or butene are oligomerized according to processes described herein, a unique mixture of liquid hydrocarbon products are formed. More particularly, this mixture of hydrocarbons may comprise at least 95% by weight of mono-olefin oligomers of the empirical formula $$C_{(n+nm)}H_{2(n+nm)}$$

where n is 3 or 4 and m is an integer from 1 to 6, said mono-olefin oligomers comprising at least 20 percent by weight of olefins having at least 12 carbon atoms, said olefins having at least 12 carbon atoms having an average of from 0.80 to 2.00 methyl side groups per carbon chain, said olefins not having any side groups other than methyl.

It will be understood that methyl side groups are methyl groups which occupy positions other than the terminal positions of the first and last (i.e., alpha and omega) carbon atoms of the longest carbon chain. This longest carbon chain is also referred to herein as the straight backbone chain of the olefin. The average number of methyl side groups for the $C_{12}{}^+$ olefins may comprise any range within the range of 0.80 to 2.00, e.g., from 0.80 to 1.90, e.g., from 0.80 to 1.80, e.g. from 0.80 to 1.70, e.g., from 0.80 to 1.60, e.g., from 0.80 to 1.50, e.g., from 0.80 to 1.40, e.g., from 0.80 to 1.30, etc.

These oligomers may be separated into fractions by conventional distillation separation. When propylene is oligomerized, olefin fractions containing the following numbers of carbon atoms can be obtained: 6, 9, 12, 15, 18 and 21. When butene is oligomerized, olefin fractions containing the following numbers of carbon atoms may be obtained: 8, 12, 16, 20, 24 and 28. It is also possible to oligomerize a mixture of propylene and butene and to obtain a mixture of oligomers having at least 6 carbon atoms.

By fractionating an oligomerization product prepared by processes described herein, one may obtain a mixture of hydrocarbons, said hydrocarbons comprising at least 95 (e.g., at least 98) percent by weight of mono-olefins having 12 carbon atoms, said mono-olefins having a straight backbone chain of at least 10 carbon atoms, said mono-olefins having an average of from 0.40 to 2.00 (e.g., from 0.50 to 1.90, e.g., from 0.60 to 1.80, e.g., from 0.70 to 1.70, e.g., from 0.80 to 1.60, e.g., from 0.80 to 1.50, e.g., from 0.80 to 1.40, e.g., from 0.80 to 1.30) methyl side groups per carbon chain. These $C_{12}$ olefins may comprise or consist essentially of at least 5 (e.g., from 5 to 40, e.g., from 5 to 25) mole percent dodecene (i.e., a $C_{12}$ olefin having no methyl side groups), at least 30 (e.g., from 30 to 90, e.g., from 65 to 80) mole percent methylundecene (i.e., a $C_{12}$ olefin having one methyl side group) and at least 5 (e.g., from 5 to 40, e.g., from 5 to 25) mole percent dimethyldecene (i.e., a $C_{12}$ olefin having two methyl side groups).

Another hydrocarbon fractionation product may be a mixture of hydrocarbons, said hydrocarbons comprising at least 95 (e.g., at least 98) percent by weight of mono-olefins having 15 carbon atoms, said mono-olefins having a straight backbone chain of at least 13 carbon atoms, said mono-olefins having an average of from 0.40 to 2.00 (e.g., from 0.50 to 1.90, e.g., from 0.60 to 1.80, e.g., from 0.70 to 1.70, e.g., from 0.80 to 1.60, e.g., from 0.80 to 1.50, e.g., from 0.80 to 1.40, e.g., from 0.80 to 1.30) methyl side groups per carbon chain. These $C_{15}$ olefins may comprise or consist essentially of at least 5 (e.g., from 5 to 40, e.g., from 5 to 25) mole percent pentadecene (i.e., a $C_{15}$ olefin having no methyl side groups) at least 30 (e.g., from 30 to 90, e.g., from 65 to 80) mole percent methyltetradecene (i.e., a $C_{15}$ olefin having one methyl side group) and at least 5 (e.g., from 5 to 40, e.g., from 5 to 25) mole percent dimethyltridecene (i.e., a $C_{15}$ olefin having two methyl side groups).

Another hydrocarbon fractionation product may be a mixture of hydrocarbons, said hydrocarbons comprising at least 95 (e.g., at least 98) percent by weight of mono-olefins having 16 carbon atoms, said mono-olefins having a straight backbone chain of at least 14 carbon atoms, said mono-olefins having an average of from 0.40 to 2.00 (e.g., from 0.50 to 1.90, e.g., from 0.60 to 1.80, e.g., from 0.70 to 1.70, e.g., from 0.80 to 1.60, e.g., from 0.80 to 1.50, e.g., from 0.80 to 1.40, e.g., from 0.80 to 1.30) methyl side groups per carbon chain. These $C_{16}$ olefins may comprise or consist essentially of at least 5 (e.g., from 5 to 40, e.g., from 5 to 25) mole percent hexadecene (i.e., a $C_{16}$ olefin having no methyl side groups) at least 30 (e.g., from 30 to 90, e.g., from 65 to 80) mole percent methylpentadecene (i.e., a $C_{16}$ olefin having one methyl side group) and at least 5 (e.g., from 5 to 40, e.g., from 5 to 25) mole percent dimethyltetradecene (i.e., a $C_{16}$ olefin having two methyl side groups).

Another hydrocarbon fractionation product may be a mixture of hydrocarbons, said hydrocarbons comprising at least 95 (e.g., at least 98) percent by weight of mono-olefins having 18 carbon atoms, said mono-olefins having a straight backbone chain of at least 16 carbon atoms, said mono-olefins having an average of from 0.40 to 2.00 (e.g., from 0.50 to 1.90, e.g., from 0.60 to 1.80, e.g., from 0.70 to 1.70, e.g., from 0.80 to 1.60, e.g., from 0.80 to 1.50, e.g., from 0.80 to 1.40, e.g., from 0.80 to 1.30) methyl side groups per carbon chain. These $C_{18}$ olefins may comprise or consist essentially of at least 5 (e.g., from 5 to 40, e.g., from 5 to 25) mole percent octadecene (i.e., a $C_{18}$ olefin having no methyl side groups) at least 30 (e.g., from 30 to 90, e.g., from 65 to 80) mole percent methylheptadecene (i.e., a $C_{18}$ olefin having one methyl side group) and at least 5 (e.g., from 5 to 40, e.g., from 5 to 25) mole percent dimethylhexadecene (i.e., a $C_{18}$ olefin having two methyl side groups).

These olefin mixtures, particularly the above-mentioned fractionation products, may be used as is or may be blended with other olefin such as various straight chain olefins (i.e. olefins having no methyl side groups) to provide further olefin mixtures.

One use for olefin oligomers described herein, particularly $C_{12}$ fractions of the oligomers, is as alkylating agents in a process for the selective alkylation of an aromatic compound (e.g., benzene) with a relatively long chain length alkylating agent to produce substantially linear phenylalkanes. Catalysts and reaction conditions for this alkylation process are disclosed in the aforementioned U.S. Pat. No. 4,301,317, which describes a similar alkylation process using linear olefins (e.g., dodecene) as alkylating agents.

It has now been discovered that the reaction of aromatic compounds with the present long-chain oligomers, when carried out in the presence of certain crystalline zeolite materials as catalysts, will result in linear phenylalkanes in which the content of 2-phenyl substituted linear alkane isomer is believed to be in excess of its expected equilibrium concentration. The crystalline zeolites utilizable in this process are characterized by channels or networks of pores therethru, the major dimension of the opening to the channels or networks of pores being between about 6 angstrom units and about 7 angstrom units. Specific preferred catalysts include cancrinite, gmelinite, mordenite, and offretite and synthetic and naturally occurring isotypes thereof. A particularly preferred zeolite is dealuminized mordenite.

The alkylation process is carried out by contacting the aromatic compound, which may be a substituted or unsubstituted benzene, with the alkylating agent in the presence of the specified type of zeolite catalyst and under suitable alkylation conditions. Preferred conditions include a temperature of between about 50° C. and 500° C. and a pressure of about $2.5 \times 10^4$ N/m$^2$ to $2.5 \times 10^7$ N/m$^2$ (0.25–250 atmospheres).

The aromatic compounds which are to be reacted with the foregoing alkylating agents to yield phenylalkanes by the process disclosed herein are benzene compounds. These benzene compounds may be unsubstituted, or they may carry from 1 to 2 substituents on the ring structure. If substituted, the substituent may be an alkyl group having from 1 to 10 carbon atoms therein, or may be a halide, an alkoxy, an aryl group, and so forth, or any combination of such substituents.

The zeolites utilized in the alkylation process disclosed herein may be either naturally occurring or synthetic and include, by way of example, cancrinite, gmelinite, mordenite, dealuminized mordenite and offretite. Also contemplated as being included herein are synthetic and naturally occurring isotypes of such zeolite materials, such as: zeolite S, zeolite NaS, zeolite NaD, Ptilolite, Zeolon, zeolite O, TMA-offretite, and others.

The crystal structure of the class of zeolites suitable for use as catalysts in the alkylation process is such as to provide access to and egress from the intracrystalline free space of the zeolites by virtue of having channels or networks of pores (hereinafter referred to as pores), the openings thereto preferably having a major dimension of between about 6A and about 7A. The zeolites utilized in the alkylation process discussed herein are further characterized by pore apertures of about a size as would be provided by 12-member rings of silicon or aluminum atoms. It will be understood, of course, that these rings are those formed by the regular disposition of the tetrahedra making up the anionic framework of the crystalline zeolite, the silicon or aluminum atoms forming the centers of the tetrahedra and being themselves bonded together by oxygen atoms.

The pores characterizing the zeolites useful in the present alkylation process may be substantially circular, such as is the situation with respect to cancrinite which has uniform pores of about 6.2 angstroms, or may be somewhat elliptical, such as mordenite. It should be understood that, in any case, the zeolites used as catalysts in the alkylation process have a major pore dimension intermediate between that of the large pore zeolites, such as the X and Y zeolites, and the relatively small pore size zeolites ZSM-5 and ZSM-11, and preferably between about 6A and about 7A. The pore size dimensions and crystal structures of certain zeolites are specified in Atlas of Zeolite Structure Types by W. M. Meier and D. H. Olson, published by the Structure Commission of the International Zeolite Association (1978) and distributed by Polycrystal Book Service, Pittsburgh, Pa.

The zeolites useful in the alkylation process generally have at least 10 percent of the cationic sites thereof occupied by ions other than alkali or alkaline-earth metals. Typical but non-limiting replacing ions including ammonium, hydrogen, rare earth, zinc, copper and aluminum. Of this group, particular preference is accorded ammonium, hydrogen, rare earth or combinations thereof. In a preferred embodiment, the zeolites are converted to the predominantly hydrogen form, generally by replacement of the alkali metal or other ion originally present with hydrogen ion precursors, e.g., ammonium ions, which upon calcination yield the hydrogen form. This exchange is conveniently carried out by contact of the zeolite with an ammonium salt solution, e.g., ammonium chloride, utilizing well known ion exchange techniques. The extent of replacement is such as to produce a zeolite material in which at least 50 percent of the cationic sites are occupied by hydrogen ions.

The zeolites may be subjected to various chemical treatments, including alumina extraction and combination with one or more metal components, particularly the metals of Groups IIB, III, IV, VI, VII and VIII. It is also contemplated that the zeolites may, in some instances, desirably be subjected to thermal treatment, including steaming or calcination in air, hydrogen or an inert gas, e.g. nitrogen or helium.

An especially useful modifying treatment entails steaming of the zeolite by contact with an atmosphere containing from about 5 to about 100 percent steam at a temperature of from about 250° to 1000° C. Steaming may last for a period of between about 0.25 and about 100 hours and may be conducted at pressures ranging from sub-atmospheric to several hundred atmospheres to reduce the alpha value of the zeolite to less than 500, and preferably less than 20, but greater than zero.

In practicing the desired alkylation process, it may be useful to incorporate the above-described intermediate pore size crystalline zeolites in another material resistant to the temperature and other conditions employed in the process. Such matrix materials include synthetic or naturally occurring substances as well as inorganic materials such as clay, silica, and/or metal oxides. The latter may be either naturally occurring or in the form of gels or gelatinous precipitates including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituents in halloysite, kaolinite, dickite, nacrite or anauxite. Such clays can be used in the raw state as originally mined or initially subjected to calcination, acid treatment or chemical modification.

In addition to the foregoing materials, the intermediate pore size zeolites employed herein may be compounded with a porous matrix material, such as alumina, silica-alumina, silica-magnesia, silica-zirconia, silica-thoria, silica-beryllia, and silica-titania, as well as ternary combinations, such as silica-alumina-thoria, silica-alumina-zirconia, silica-alumina-magnesia and silica-magnesia-zirconia. The matrix may be in the form of a cogel. The relative proportions of finely divided zeolite and inorganic oxide gel matrix may vary widely, with the zeolite content ranging from between about 1 to about 99 percent by weight and more usually in the range of from about 5 to about 80 percent by weight of the composite.

The alkylation process is conducted such that the organic reactants, i.e., the aromatic compound and the alkylating agent, are brought into contact with the zeolite in a suitable reaction zone, such as for example a fixed bed of the catalyst, under effective alkylation conditions. Such conditions include a temperature of between about 50° C. and about 500° C., a pressure of between about $2.5 \times 10^4 \, N/m^2$ and about $2.5 \times 10^7 \, N/m^2$ (0.25–250 atmospheres), and a feed weight hourly space velocity (WHSV) of between about 0.1 and about 500. The latter WHSV is based upon the weight of the catalyst compositions employed, i.e. the total weight of active catalyst and binder therefor. Preferred reaction conditions include a temperature within the appropriate range of 100° C. to 350° C. with a feed WHSV of between 5.0 and 100. Although the reaction normally takes place at atmospheric pressure ($10^5 \, N/m^2$), the preferred pressure range extends from about $10^5 \, N/m^2$ to about $5 \times 10^6 \, N/m^2$. The reactants may be in either the vapor phase or the liquid phase and may be neat, i.e., free from intentional admixture or dilution with other material, or may be brought into contact with the zeolite with the aid of carrier gases or diluents such as, for example, hydrogen or nitrogen.

The alkylation process described herein may be carried out as a batch-type, semi-continuous or continuous operation utilizing a fixed or moving bed catalyst system. A preferred embodiment entails use of a catalyst zone wherein the hydrocarbon charge is passed concurrently or countercurrently through a moving bed of particle-form catalyst. The latter, after use, is conducted to a regeneration zone where coke is burned from the catalyst in an oxygen-containing atmosphere (such as air) at elevated temperature, after which the regenerated catalyst is recycled to the conversion zone for further contact with the organic reactants.

The alkylbenzenes prepared by the above-discussed alkylation process are useful as intermediates for the production of alkylphenylsulfonates, which are useful as detergents or surfactants. Processes for sulfonating alkylbenzenes are described in the aforementioned U.S. Pat. No. 4,298,547. More particularly, alkylbenzenes may be converted to alkylphenylsulfonates by sulfonation of the aromatic ring with sulfuric acid. The reaction is well known in the art and is commonly carried out by contacting the organic compound with sulfuric acid at temperatures of from about −70° C. to about +60° C. Detailed descriptions of specific commercial processes abound in the literature—see, for instance, pages 60–62 of Industrial Chemicals, Third Edition, by W. L. Faith et al, published by John Wiley & Sons, Inc., 1966—and those skilled in the field need only refer to the conventional literature for instruction on how to carry out such reactions.

There are a number of surprising features about the present alkylation process, as well as about the alkylbenzene and alkylphenylsulfonate products. First it will be noted that the active catalytic sites of zeolite catalysts have general acid catalytic activity and are not specific to promoting only the alkylation of aromatics. Possible side reactions which could also be promoted, given the present reactants and products, include, e.g., cracking, aromatization, dealkylation and oligomerization. Although U.S. Pat. No. 4,301,317 shows that dealuminized mordenite will successfully catalyze the alkylation of benzene with a straight long chain olefin, such as 1-dodecene, having no methyl side groups, prior to the present alkylation process it was uncertain what effect the presence of a significant number of methyl side groups would have on the reaction. For example, one might have speculated that the bulky alkylbenzene product, if formed, would diffuse too slowly out of the pores of the zeolite and would tend to become reconverted therein into cracked or dealkylated by-products. The present alkylation was found to proceed much slower than a corresponding alkylation with a straight chain olefin, but the selectivity of the present alkylation reaction to the desired alkylbenzene product was surprisingly high. By way of contrast, a zeolite beta catalyst produced a product containing less than 20 percent (by GC peak area) alkylbenzene and more than 80 percent of an olefin by-product, even when 1-dodecene was used as the alkylating agent. When a more highly branched olefin alkylating agent (e.g., containing much more branching than the present olefin alkylating agent) was used, an alkylbenzene product was not obtained even when a dealuminized mordenite catalyst was used.

Another surprising feature of the present alkylation process is that it leads to alkylbenzenes and alkylphenylsulfonates which have a surprising degree of biodegradability. Given the complexity of the reactants used and possible isomerization reactions which can take place during the present alkylation reactions, it will be understood that the present alkylbenzene and alkylphenylsulfonate products represent a complex mixture of different products. Portions of a hook by R. D. Swisher, entitled *Surfactant Biodegradation*, Marcel Dekker, Inc., New York, 1970, pp 203–231 (note especially pp. 220–223) discuss the effect on biodegradability of methyl groups on alkyl chains of certain specific alkylbenzenesulfonates. However, it is quite difficult to predict the biodegradability of a complex mixture of isomers such as the present alkylphenylsulfonate products. It was necessary to first make these materials and then actually test them before a reasonable assessment of their biodegradability could be made.

EXAMPLE I

Aluminosilicate H-ZSM-23 extrudate (65% zeolite, 35% alumina binder) is loaded into a metal pressurized reactor and calcined overnight at 500° C. The catalyst is then used to oligomerize propylene to intermediate molecular weight olefins. Various temperatures and feed rates are employed. These results are summarized in Table 1.

TABLE 1

| Propylene Oligomerization with HZSM-23 | | | | |
|---|---|---|---|---|
| Run No. | $C_3=$ WHSV | Temp. °C. | $C_{12}+$ Select wt. %[a] | Branching Index[b] | Branching Methyls[b] per $C_{15}$ |
| 1-A | 1.0 | 160 | 61.5 | 51.7 | 3.5 |

TABLE 1-continued

Propylene Oligomerization with HZSM-23

| Run No. | $C_3=$ WHSV | Temp. °C. | $C_{12}+$ Select. wt. %[a] | Branching Index[b] | Branching Methyls[b] per $C_{15}$ |
|---|---|---|---|---|---|
| 1-B | 0.5 | 160 | 73.7 | 51.4 | 3.5 |
| 1-C | 0.5 | 200 | 78.6 | 54.7 | 3.8 |
| 1-D | 1.0 | 200 | 81.7 | 55.1 | 3.9 |
| 1-E | 1.0 | 225 | 78.5 | 52.3 | 3.6 |

[a] crude reaction product
[b] $C_{12}+$ fraction

The determination of Branching Index is a useful and sensitive method practiced by those skilled in the arts to which the present invention applies and used to quantitatively assess the degree of linearity of a molecule or molecular mixture. The index is determined as follows: the C6 and C9 oligomers are first removed from the sample and the C12+ fraction is hydrogenated using Pd/charcoal catalyst in acetic acid. The hydrogenated sample is extracted from the acetic acid into deutrochloroform and the 1H NMR spectrum determined. The branching index is defined as the ratio of the intensity (area) of the resonance due to CH3 (0.7–1.0 ppm) divided by the sum of the intensities (areas) of the resonances due to CH3 (0.7–1.0 ppm) and CH2 (1.1–1.8 ppm). The number of methyl groups per molecule is defined by the equation $$\text{Me/molecule} = \text{B.I.}*(n+1))/150$$

where
B.I.=branching index as defined above and
n=carbon number of the fraction of interest.

This calculated number of methyls per molecule includes the two terminal methyl groups. Therefore, to determine the actual number of methyl side groups, e.g., mid-chain methyl groups, these two terminal methyl groups must be subtracted from the total methyl/molecule value calculated.

EXAMPLE II

The catalyst used in Example I is calcined in the reactor overnight at 500° C. The calcined catalyst is then cooled to room temperature in the reactor, and a solution containing 1 gram 2,6-di-t-butyl pyridine per 100 ml pentane is passed over the catalyst until a total of 6 ml of deactivating solution per gram of catalyst has been used. Following this treatment, the catalyst is purged with nitrogen for one hour at room temperature, then the reactor temperature is slowly increased and reaction of propylene begun. During the reaction of propylene, a small amount of 2,6-di-t-butyl pyridine (DTBP) solution is co-fed to maintain surface deactivation. The results of these screening reactions are summarized in Table 2.

TABLE 2

Propylene Oligomerization with 2,6-DTBP Modified ZSM-23

| Run No. | $C_3=$ WHSV | 2,6-DTBP ppm | Temp. °C. | $C_{12}+$ Select. wt. %[a] | Branching Index[b] | Branching Methyls[b] per $C_{15}$ |
|---|---|---|---|---|---|---|
| 2-A | 1.0 | 400 | 175 | 18.4 | 40.0 | 2.3 |
| 2-B | 0.5 | 800 | 200 | 43.8 | 39.4 | 2.2 |
| 2-C | 1.0 | 400 | 200 | 32.2 | 40.7 | 2.3 |
| 2-D | 0.5 | 800 | 220 | 50.4 | 41.9 | 2.5 |

[a] In crude reaction product
[b] In $C_{12}+$ fraction

EXAMPLE III

H-ZSM-23, prepared as in Example I is treated with deactivating soution as in Example II, except that the basic component is 2,4,6-collidine. A small co-feed of 2,4,6-collidine solution is continued during reaction to maintain surface deactivation. Results of these reactions are summarized in Table 3.

TABLE 3

Propylene Oligomerization with 2,4,6-Collidine Modified ZSM-23

| Run No. | $C_3=$ WHSV | 2,4,6-Coll., ppm | Temp. °C. | $C_{12}+$ Select. wt. %[a] | Branching Index[b] | Branching Methyls[b] per $C_{15}$ |
|---|---|---|---|---|---|---|
| 3-A | 0.5 | 200 | 200 | 24.7 | 35.5 | 1.8 |
| 3-B | 0.25 | 400 | 200 | 35.1 | 34.9 | 1.7 |
| 3-C | 0.25 | 400 | 212 | 39.7 | 37.2 | 2.0 |
| 3-D | 0.25 | 400 | 225 | 33.5 | 37.6 | 2.0 |
| 3-E | 0.25 | 200 | 225 | 36.4 | 40.4 | 2.3 |

[a] In crude reaction product
[b] In $C_{12}+$ fraction

The above experimental runs are conducted at a pressure of about 3500–4300 kPa (500–600 psig.). Comparative examples run at equivalent space velocity and temperature (e.g., 0.5 WHSV and 200° C.) show significant improvement in product linearity employing the trialkylpyridine agent.

EXAMPLE IV

Propylene is contacted according to the procedure of Example I with 2,4,6-collidine modified HZSM-23 in a flow reactor at 200° C. at the rate of 0.25 g propylene/g zeolite/hr. The crude product is distilled to obtain a $C_{15}+$ fraction. The $C_{15}+$ fraction is contacted with $BF_3$/70% aqueous phosphoric acid catalyst at room temperature for about 4 hours. The crude product, containing about 75 wt% of $C_{25}+$ lube range hydrocarbon is stripped to remove the $C_{24}-$ hydrocarbons. The viscosity index of $C_{25}+$ fraction is 128; the 100° C. viscosity is 8.2 cSt.

In the multistage process 70% aqueous phosphoric acid in combination with $BF_3$ is superior to other $BF_3$/promoter combinations for converting $C_{10}-C_{20}$ intermediate olefins to lube-range hydrocarbons.

EXAMPLE V 15.4 gms HZSM-5 (65% zeolite, 35% alumina binder) are treated with 0.18 grams 2,4,6-collidine in approximately 50 cc pentane. This represents 0.25 moles amine per mole of acid in the zeolite. The pentane is allowed to evaporate at room temperature and the surface modified catalyst charged to a fixed bed tubular reactor at superatmospheric pressure. Propylene is metered to the reactor and a solution of 1 gram 2,4,6-collidine in 500 ml pentane is also metered to the reactor. The rate is controlled to give approximately 0.2 mmoles amine per mole H+ in the zeolite per hour. Reaction temperature is adjusted in an effort to achieve 50% propylene conversion.

| TEMP | 205° C. |
|---|---|
| PRESSURE | 3600 kPa (500 psig) |
| C3 = WHSV, HR-1 | 0.21 |
| DEACTIVATING AGENT IN FEED | 65 ppm |
| C3 = CONV, WT % | 55.0 |
| C12+ SELECTIVITY | 20.1% |
| C15+ | 5.9 |

-continued

| | |
|---|---|
| BRANCHING INDEX | 32.8 |
| BRANCHING METHYLS PER C15 | 1.5 |

-continued

| | |
|---|---|
| BRANCHING INDEX | 30.5 |
| BRANCHING METHYLS PER C15 | 1.25 |

EXAMPLE VI

Example V is repeated, except that 15.4 gms ZSM-5 (65% zeolite, 35% alumina binder) are treated with a solution containing 0.28 grams, 2,6-di-t-butylpyridine in pentane. (0.25 moles amine per mole H+ in the zeolite). Comparative results are summarized as follows:

| | |
|---|---|
| TEMP | 145° C. |
| PRESSURE | 3600 kPa |
| C3 = WHSV, HR-1 | 0.22 |
| AMINE IN FEED | 100 ppm |
| C3 = CONVERSION, WT % | 59.1 |
| C12+ SELECTIVITY | 9.8 |
| BRANCHING INDEX | 38.4 |
| BRANCHING METHYLS PER C15 | 2.1 |

EXAMPLE VII

Example V is repeated, except 15.4 gms HZSM-23 (65% zeolite, 35% alumina binder) are treated with 0.088 gms, 2,4,6-collidine in approximately 50 ml pentane. (0.25 moles amine per mole H+ in the zeolite.) Screening is carried at various conditions with an effort to achieve 50% propylene conversion. Results are summarized as follows:

| | |
|---|---|
| TEMP | 175° C. |
| PRESSURE | 3600 kPa |
| C3 = WHSV, HR-1 | 0.21 |
| AMINE IN FEED | 200 ppm |
| C3 = CONVERSION, WT % | 57.7 |
| C12+ SELECTIVITY | 22.0 |

EXAMPLE VIII

Example VII is repeated, except 15.4 gms ZSM-23 (65% zeolite, 35% alumina binder) are treated with 0.14 gms, 2,6-di-t-butylpyridine in approximately 50 ml pentane. (0.25 moles amine per mole H+ in the zeolite.) Results are summarized as follows:

| | |
|---|---|
| TEMP | 145° C. |
| PRESSURE | 3600 kPa |
| C3 = WHSV, HR-1 | 0.21 |
| AMINE IN FEED | 50 ppm |
| C3 = CONVERSION, WT % | 59.0 |
| C12+ SELECTIVITY | 21.6 |
| BRANCHING INDEX | 31.4 |
| BRANCHING METHYLS PER C15 | 1.35 |

EXAMPLE IX 15.4 gms HZSM-23 extrudate (65% zeolite, 35% alumina binder) were treated with 0.175 grams, 2,4,6-collidine in approximately 50 cc pentane. This HZSM-23 had a silica to alumina ratio of approximately 110 and an alpha value of about 25. The pentane was allowed to evaporate at room temperature, and the surface modified catalyst was charged to a fixed bed tubular reactor. Propylene was metered to the reactor, and a solution of 2,4,6-collidine in pentane was also metered to the reactor at 200 ppm of 2,4,6-collidine per weight of total feed into the reactor. The reaction was started at temperatures lower than that required for complete conversion in order to study the effect of incomplete propylene conversion on product quality.

Results are summarized in Tables 4 and 5.

TABLE 4

| CATALYST ACTIVITIES AND PRODUCT DISTRIBUTIONS OBSERVED IN FIXED BED FLOW REACTIONS | | | | | | | | | | | | | | | |
|---|---|---|---|---|---|---|---|---|---|---|---|---|---|---|---|
| RUN NUMBER | 9-A | 9-B | 9-C | 9-D | 9-E | 9-F | 9-G | 9-H | 9-I | 9-J | 9-K | 9-L | 9-M | 9-N | 9-O |
| REACT COND | | | | | | | | | | | | | | | |
| TOS, DAYS | 1 | 2 | 3 | 6 | 7 | 9 | 10 | 13 | 14 | 15 | 16 | 17 | 20 | 21 | 22 |
| TEMP, C. | 200 | 200 | 200 | 205 | 205 | 205 | 210 | 215 | 215 | 215 | 220 | 220 | 220 | 225 | 230 |
| PRESSURE, PSIG | 540 | 540 | 540 | 540 | 540 | 540 | 540 | 540 | 540 | 540 | 540 | 540 | 540 | 540 | 540 |
| $C_3$ = WHSV, $HR^{-1}$ | 0.22 | 0.22 | 0.22 | 0.23 | 0.48 | 0.23 | 0.24 | 0.22 | 0.22 | 0.26 | 0.22 | 0.24 | 0.22 | 0.25 | 0.23 |
| POISON, PPM | 200 | 200 | 200 | 200 | 200 | 200 | 200 | 200 | 200 | 200 | 200 | 200 | 200 | 200 | 200 |
| PROD DIST, WT % | | | | | | | | | | | | | | | |
| $C_6$ | 37.0 | 34.6 | 39.6 | 54.2 | 45.8 | 49.2 | 52.2 | 55.6 | 56.8 | 49.2 | 51.8 | 57.0 | 54.4 | 61.9 | 54.1 |
| $C_9$ | 31.4 | 30.3 | 25.8 | 20.5 | 25.2 | 24.3 | 22.4 | 21.1 | 20.5 | 23.8 | 22.7 | 21.3 | 23.6 | 20.7 | 20.4 |
| $C_{12}$ | 19.1 | 22.1 | 18.3 | 12.1 | 15.3 | 14.5 | 13.3 | 12.1 | 11.8 | 14.2 | 13.5 | 11.7 | 12.4 | 10.8 | 13.6 |
| $C_{15}$ | 6.7 | 10.3 | 9.6 | 6.9 | 7.9 | 8.0 | 7.1 | 6.9 | 6.8 | 7.9 | 7.4 | 6.8 | 6.6 | 4.5 | 7.8 |
| $C_{18}$ | 1.3 | 2.4 | 4.0 | 3.2 | 3.5 | 2.6 | 2.7 | 2.9 | 3.0 | 3.1 | 2.9 | 2.6 | 2.1 | 1.4 | 2.9 |
| $C_{21}^+$ | 4.4 | 0.4 | 2.6 | 3.1 | 2.4 | 1.4 | 2.2 | 1.5 | 1.1 | 1.8 | 1.8 | 0.6 | 0.8 | 0.8 | 1.1 |
| $C_{12}^+$ SELECT, WT % | 31.6 | 35.1 | 34.6 | 25.3 | 29.1 | 26.5 | 25.3 | 23.3 | 22.7 | 27.0 | 25.5 | 21.7 | 21.9 | 17.4 | 25.5 |
| $C_{15}^+$ SELECT, WT % | 12.4 | 13.0 | 16.3 | 13.2 | 13.8 | 12.0 | 12.0 | 11.2 | 10.9 | 12.8 | 12.0 | 10.0 | 9.5 | 6.6 | 11.9 |
| PERCENT $C_3$ = CONV | 9.6 | 14.0 | 19.4 | 70.1 | 20.2 | 28.4 | 49.4 | 70.6 | 62.7 | 62.9 | 99.6 | 88.2 | 76.3 | 90.5 | 97.9 |

TABLE 5

| CARBON SKELETON DISTRIBUTIONS OBSERVED IN FIXED BED FLOW REACTIONS | | | | | | | | | | | | | | | |
|---|---|---|---|---|---|---|---|---|---|---|---|---|---|---|---|
| RUN NUMBER | 9-A | 9-B | 9-C | 9-D | 9-E | 9-F | 9-G | 9-H | 9-I | 9-J | 9-K | 9-L | 9-M | 9-N | 9-O |
| REACT COND | | | | | | | | | | | | | | | |
| TOS, DAYS | 1 | 2 | 3 | 6 | 7 | 9 | 10 | 13 | 14 | 15 | 16 | 17 | 20 | 21 | 22 |
| TEMP, C. | 200 | 200 | 200 | 205 | 205 | 205 | 210 | 215 | 215 | 215 | 220 | 220 | 220 | 225 | 230 |
| PRESSURE, PSIG | 540 | 540 | 540 | 540 | 540 | 540 | 540 | 540 | 540 | 540 | 540 | 540 | 540 | 540 | 540 |
| $C_3$ = WHSV, $HR^{-1}$ | 0.22 | 0.22 | 0.22 | 0.23 | 0.48 | 0.23 | 0.24 | 0.22 | 0.22 | 0.26 | 0.22 | 0.24 | 0.22 | 0.25 | 0.23 |
| POISON, PPM | 200 | 200 | 200 | 200 | 200 | 200 | 200 | 200 | 200 | 200 | 200 | 200 | 200 | 200 | 200 |

TABLE 5-continued

CARBON SKELETON DISTRIBUTIONS OBSERVED IN FIXED BED FLOW REACTIONS

| RUN NUMBER | 9-A | 9-B | 9-C | 9-D | 9-E | 9-F | 9-G | 9-H | 9-I | 9-J | 9-K | 9-L | 9-M | 9-N | 9-O |
|---|---|---|---|---|---|---|---|---|---|---|---|---|---|---|---|
| CARBON SKELETON | | | | | | | | | | | | | | | |
| $C_9$ | | | | | | | | | | | | | | | |
| ≧DI-ME (A) | 7.3 | 5.5 | 5.8 | 9.2 | 6.5 | 7.5 | 8.2 | 9.7 | 9.6 | 11.9 | 12.0 | 15.3 | 11.3 | 13.6 | 15.3 |
| MONO-ME | 62.0 | 65.8 | 68.0 | 75.1 | 72.4 | 73.1 | 73.4 | 74.1 | 74.8 | 73.5 | 76.4 | 72.7 | 75.9 | 75.1 | 74.8 |
| NORMAL | 30.6 | 28.8 | 26.2 | 15.7 | 21.2 | 19.4 | 18.5 | 16.3 | 15.7 | 14.6 | 11.6 | 12.0 | 12.8 | 11.3 | 9.9 |
| ME/$C_9$ (B) | 0.80 | 0.80 | 0.82 | 0.98 | 0.89 | 0.92 | 0.94 | 0.98 | 0.99 | 1.03 | 1.06 | 1.11 | 1.04 | 1.09 | 1.13 |
| $C_{12}$ | | | | | | | | | | | | | | | |
| ≧DI-ME | 9.7 | 10.3 | 10.3 | 14.8 | 12.6 | 13.9 | 13.7 | 15.6 | 16.1 | 16.1 | 19.2 | 18.5 | 18.3 | 19.6 | 21.5 |
| MONO-ME | 69.9 | 74.1 | 75.2 | 75.4 | 76.3 | 76.0 | 75.9 | 75.8 | 74.8 | 74.6 | 72.5 | 72.6 | 73.7 | 72.3 | 70.7 |
| NORMAL | 20.3 | 15.6 | 14.5 | 9.8 | 11.1 | 10.1 | 10.5 | 8.6 | 9.1 | 9.2 | 8.3 | 8.9 | 8.1 | 8.0 | 7.9 |
| ME/$C_{12}$ | 0.94 | 1.00 | 1.01 | 1.12 | 1.08 | 1.11 | 1.10 | 1.15 | 1.15 | 1.15 | 1.20 | 1.19 | 1.19 | 1.21 | 1.24 |
| $C_{15}$ | | | | | | | | | | | | | | | |
| ≧DI-ME | 12.5 | 13.5 | 14.4 | 19.4 | 16.6 | 18.4 | 18.3 | 26.6 | 20.3 | 20.1 | 20.8 | 23.0 | 23.4 | 23.4 | 24.4 |
| MONO-ME | 73.4 | 77.3 | 78.3 | 74.9 | 76.8 | 75.2 | 76.1 | 69.5 | 73.4 | 73.3 | 71.7 | 70.6 | 71.2 | 70.6 | 68.6 |
| NORMAL | 14.2 | 9.2 | 7.2 | 5.6 | 6.6 | 6.3 | 5.6 | 3.9 | 6.3 | 6.6 | 7.5 | 6.4 | 5.4 | 6.0 | 7.0 |
| ME/$C_{15}$ | 1.05 | 1.11 | 1.14 | 1.24 | 1.18 | 1.21 | 1.22 | 1.36 | 1.24 | 1.24 | 1.24 | 1.28 | 1.80 | 1.29 | 1.30 |

(A) All values for isomer distributions are normalized percentages for that carbon number
(B) Values for number of methyl branches were calculated assuming an average of 2.5 for ≧ di-methyl component In Table 4, TOS stands for time on stream. In Table 5, ≧DI-ME stands for olefins having two or more methyl side groups per chain, MONO-ME stands for olefins having one methyl side group per chain, and NORMAL stands for olefins having no methyl side groups per chain.

As propylene conversion increases (by increasing temperature), a concomitant increase in branching has been observed. For example, at 30% conversion, there may be an average of 1.0 methyl branches in the $C_{12}$ fraction. At 99% conversion, branching may increase to 1.25 methyl branches in the $C_{12}$'s.

Under conditions giving incomplete propylene conversion, distribution of product oligomers does not appear to be significantly affected by changes in propylene conversion. Single-pass selectivities to the $C_{12+}$ fraction are generally 25–30%. Oligomers formed under these conditions are almost exclusively discrete multiples of three carbon atoms indicating little cracking is occurring at these temperatures.

EXAMPLE X

In accordance with this Example, reaction temperature was increased beyond that necessary to give complete propylene conversion. 15.4 grams HZSM-23 extrudate (65% zeolite, 35% alumina binder) were treated with 0.088 grams 2,4,6-collidine in approximately 50 cc pentane. The HZSM-23 had a silica to alumina ratio of approximately 110 and an alpha value of about 25. The pentane was allowed to evaporate, and the surface modified catalyst was charged to a fixed bed tubular reactor. Propylene was metered to the reactor, and a solution of 2,4,6-collidine in pentane was also metered to the reactor at 200 ppm of 2,4,6-collidine per weight of total feed into the reactor. Results are summarized in Tables 6 and 7.

TABLE 6

PRODUCT DISTRIBUTIONS OBSERVED AT HIGHER REACTION TEMPERATURES

| RUN NUMBER | 10-A | 10-B | 10-C | 10-D | 10-E | 10-F | 10-G | 10-H | 10-I | 10-J | 10-K | 10-L | 10-M |
|---|---|---|---|---|---|---|---|---|---|---|---|---|---|
| REACT COND | | | | | | | | | | | | | |
| TEMP (SETTING) | 175 | 180 | 1 | 190 | 195 | 205 | 210 | 215 | 220 | 225 | 230 | 240 | 255 |
| TEMP (HOT SPOT) | 196 | 206 | 214 | 219 | 237 | 236 | 242 | 251 | 254 | 258 | 258 | 272 | 290 |
| PRESSURE, PSIG | 500 | 500 | 500 | 500 | 495 | 495 | 495 | 490 | 490 | 520 | 510 | 510 | 500 |
| $C_3$ = WHSV | 0.22 | 0.24 | 0.24 | 0.23 | 0.21 | 0.19 | 0.21 | 0.20 | 0.19 | 0.17 | 0.17 | 0.31 | 0.22 |
| POISON, PPM | 200 | 200 | 200 | 200 | 200 | 200 | 200 | 200 | 200 | 200 | 200 | 200 | 200 |
| PROD DIST | | | | | | | | | | | | | |
| $C_6$ | 51.6 | 60.1 | 58.7 | 51.1 | 35.7 | 35.3 | 29.2 | 25.9 | 25.9 | 19.4 | 20.9 | 16.2 | 16.7 |
| $C_9$ | 22.1 | 19.1 | 20.1 | 21.4 | 20.4 | 19.4 | 18.2 | 18.1 | 18.3 | 19.2 | 17.8 | 20.9 | 24.8 |
| $C_{12}$ | 13.2 | 10.0 | 11.0 | 13.3 | 20.6 | 18.9 | 20.7 | 22.2 | 23.3 | 24.3 | 22.7 | 23.9 | 24.1 |
| $C_{15}$ | 8.5 | 6.1 | 6.4 | 8.7 | 13.5 | 13.5 | 15.5 | 17.1 | 17.6 | 19.5 | 18.9 | 19.5 | 17.6 |
| $C_{18}$ | 3.3 | 2.8 | 2.4 | 3.4 | 5.5 | 8.0 | 9.6 | 10.2 | 10.0 | 11.8 | 12.9 | 13.4 | 11.1 |
| $C_{21}^+$ | 1.3 | 1.9 | 1.4 | 2.2 | 4.4 | 4.9 | 6.0 | 5.7 | 4.2 | 5.7 | 6.8 | 6.1 | 5.7 |
| $C_{12}^+$ SELECT | 26.3 | 20.8 | 21.2 | 27.5 | 44.0 | 45.3 | 51.7 | 55.2 | 55.1 | 61.4 | 61.3 | 63.0 | 58.5 |
| $C_{15}^+$ SELECT | 13.1 | 10.8 | 10.2 | 14.3 | 23.4 | 26.5 | 31.0 | 33.0 | 31.8 | 37.0 | 38.7 | 39.1 | 34.3 |
| $C_3$ = CONV | 35.6 | 65.5 | 91.1 | 100.0 | 100.0 | 100.0 | 100.0 | 100.0 | 100.0 | 100.0 | 100.0 | 100.0 | 100.0 |

TABLE 7

CARBON SKELETON DISTRIBUTIONS OBSERVED AT HIGHER REACTION TEMPERATURES

| RUN NUMBER | 10-A | 10-B | 10-C | 10-D | 10-E | 10-F | 10-G | 10-H | 10-I | 10-J | 10-K | 10-L | 10-M |
|---|---|---|---|---|---|---|---|---|---|---|---|---|---|
| REACT COND | | | | | | | | | | | | | |
| TEMP (SETTING) | 175 | 180 | 185 | 190 | 195 | | | 215 | 220 | 225 | 230 | 240 | 255 |
| TEMP (HOT SPOT) | 196 | | | 219 | 237 | | | 251 | 254 | 258 | 258 | 272 | 290 |
| PRESSURE, PSIG | 500 | | 500 | | 500 | 495 | 495 | | 490 | 490 | 520 | 510 | 510 | 500 |
| $C_3$ = WHSV | | 0.24 | 0.24 | 0.23 | 0.21 | 0.19 | | 0.20 | 0.19 | 0.17 | 0.17 | 0.31 | 0.22 |
| POISON, PPM | 200 | 200 | 200 | 200 | 200 | 200 | 200 | 200 | 200 | 200 | 200 | 200 | 200 |
| CARBON SKELETON | | | | | | | | | | | | | |

TABLE 7-continued

CARBON SKELETON DISTRIBUTIONS OBSERVED
AT HIGHER REACTION TEMPERATURES

| RUN NUMBER | 10-A | 10-B | 10-C | 10-D | 10-E | 10-F | 10-G | 10-H | 10-I | 10-J | 10-K | 10-L | 10-M |
|---|---|---|---|---|---|---|---|---|---|---|---|---|---|
| $C_9$ | | | | | | | | | | | | | |
| DI-ME (a) | 7.1 | 8.9 | 11.0 | 14.0 | 40.4 | 37.5 | 49.0 | 33.6 | 55.6 | 60.7 | 60.2 | 60.3 | 58.6 |
| MONO-ME | 76.1 | 77.7 | 77.6 | 78.0 | 54.9 | 57.7 | 46.9 | 42.5 | 40.7 | 35.5 | 36.0 | 35.6 | 35.4 |
| NORMAL | 16.8 | 13.4 | 11.4 | 8.0 | 4.8 | 4.8 | 4.1 | 3.8 | 3.7 | 3.8 | 3.8 | 4.1 | 6.0 |
| ME/$C_9$ (b) | 0.94 | 1.00 | 1.05 | 1.13 | 1.56 | 1.51 | 1.69 | 1.77 | 1.80 | 1.87 | 1.87 | 1.86 | 1.82 |
| $C_{12}$ | | | | | | | | | | | | | |
| DI-ME | 14.9 | 17.0 | | 21.3 | 46.3 | 42.1 | 54.0 | 59.0 | 60.5 | 69.8 | 70.5 | 69.9 | 70.6 |
| MONO-ME | 76.9 | 75.1 | 72.7 | 75.2 | 50.1 | 54.3 | 43.0 | 38.2 | 36.9 | 27.8 | 27. | 27.6 | 25.8 |
| NORMAL | 8.2 | 7.9 | 8.7 | 6.2 | 3.7 | 3.6 | 3.0 | 2.8 | 2.7 | 2.4 | 2.2 | 2.4 | 3.6 |
| ME/$C_{12}$ | 1.14 | 1.18 | 1.19 | 1.28 | 1.66 | 1.60 | 1.78 | 1.86 | 1.88 | 2.02 | 2.04 | 2.02 | 2.02 |
| $C_{15}$ | | | | | | | | | | | | | |
| DI-ME | 22.5 | 22.7 | 22.6 | 25.2 | 54.5 | 49.9 | 60.7 | 65.7 | 66.7 | 73.0 | 74.7 | 74.6 | 71.6 |
| MONO-ME | 73.0 | 72.9 | 71.8 | 70.3 | 43.0 | 47.1 | 37.1 | 32.3 | 31.3 | 24.9 | 23.4 | 23.4 | 25.5 |
| NORMAL | 4.5 | 4.6 | 5.6 | 4.4 | 2.5 | 3.0 | 2.2 | 2.0 | 2.1 | 2.1 | 1.9 | 2.0 | 2.9 |
| ME/$C_{15}$ | 1.29 | 1.30 | 1.28 | 1.33 | 1.79 | 1.72 | 1.89 | 1.97 | 1.98 | 2.07 | 2.10 | 2.10 | 2.05 |

(a) All values for isomer distributions are normalized percentages for that carbon number
(b) Values for number of methyl branches were calculated assuming an average of 2.5 for > di-methyl component These data illustrate that it is possible to increase $C_{12+}$ selectivity to 60-65% yield by increasing reaction temperature. However, under these more severe conditions, branching in the oligomers increases to greater than 2.0 methyl per $C_{12}$. Approximately 60% $C_{12+}$ selectivity is achieved at a reaction temperature of about 250° C. and higher temperatures do not result in any significant increase. This is due to the fact that the above approximately 250° C., back-cracking of the higher oligomers with concomitant carbon number scrambling becomes a significant reaction.

In studies similar to those reported in the Examples set forth hereinabove, the effects of varying the total reaction pressure where studied. By analogy to other systems involving the oligomerization of olefins, it was anticipated that higher reaction pressures could increase the product selectivity to higher oligomers. However, higher reaction pressure was not observed to result in increased selectivity to higher molecular weight materials. Data are summarized in Tables 8 and 9.

TABLE 8

EFFECT OF REACTION PRESSURE
ON PRODUCT DISTRIBUTIONS

| $C_3 =$ Press, psig | 250 | 750 | 1250 | 250 |
|---|---|---|---|---|
| He Press, psig | 0 | 0 | 0 | 1000 |
| Wt Catalyst, gms | 7.7 | 7.7 | 7.7 | 7.7 |
| Gms Liq Prod | 12.3 | 50.1 | 44.8 | 17.9 |
| Prod Dist. wt % | | | | |
| C6 | 40.6 | 62.3 | 69.6 | 30.8 |
| C9 | 24.6 | 20.6 | 15.9 | 26.3 |
| C12 | 16.1 | 9.8 | 9.0 | 20.3 |
| C15 | 10.3 | 4.7 | 3.6 | 14.1 |
| C18 | 4.7 | 1.7 | 0.9 | 5.1 |
| C21+ | 3.8 | 0.9 | 0.9 | 3.4 |
| C12+ Select, wt % | 34.9 | 17.1 | 14.4 | 42.9 |

TABLE 9

GRAMS EACH OLIGOMER PRODUCED
AT VARIOUS PRESSURES

| $C_3 =$ Press, psig | 250 | 750 | 1250 | 250 |
|---|---|---|---|---|
| He Press, psig | 0 | 0 | 0 | 1000 |
| Gms Catalyst | 7.7 | 7.7 | 7.7 | 7.7 |
| Gms Liq Prod | 12.3 | 50.1 | 44.8 | 14.2 |
| Weight, gms | | | | |
| C6 | 5.0 | 31.2 | 31.2 | 4.4 |
| C9 | 3.0 | 10.3 | 7.1 | 3.7 |
| C12 | 2.0 | 4.9 | 4.0 | 2.9 |
| C15 | 1.3 | 2.4 | 1.6 | 2.0 |

TABLE 9-continued

GRAMS EACH OLIGOMER PRODUCED
AT VARIOUS PRESSURES

| C18 | 0.6 | 0.9 | 0.4 | 0.7 |
|---|---|---|---|---|
| C21+ | 0.5 | 0.5 | 0.4 | 0.5 |
| Gms C12+ | 4.4 | 8.7 | 6.4 | 6.1 |
| Avg Gms Hr Charged | 1.1 | 5.0 | 4.7 | 1.2 |

The data in Table 8 show that instead, selectivity to $C_{12+}$ olefins decreased dramatically as the pressure was increased from 250 psig to 750 psig. The distribution of $C_{12+}$ product decreased less dramatically when pressure was increased from 750 psig to 1250 psig. Product distributions obtained at 250 psig propylene partial pressure with a total reactor pressure of 1250 psig (1000 psig He) were also observed. Although there is a somewhat higher $C_{12+}$ selectivity at the higher pressure, the product distributions more closely resemble those obtained at 250 psig propylene, not those at 1250 psig pure propylene.

If one considers only normalized product distributions at different pressures, it appears that lower reaction pressure would be desirable to maximize $C_{12+}$ selectivity. However, the rate of formation of each oligomer with pressure must also be considered. As would be expected, higher reaction pressures give faster reaction rates. Although there is a greater percentage of the higher molecular weight oligomers produced at lower pressure, there is less of each produced. This lower rate, combined with higher branching observed at lower propylene partial pressure, suggests that higher pressures may be more desirable for preparing higher molecular weight oligomers using 2,4,6-collidine modified ZSM-23 catalysts.

EXAMPLE XI

In accordance with this Example, the effect of reaction pressure on product linearity was observed. 15.4 grams HZSM-23 extrudate (65% zeolite, 35% alumina) were treated with 2,4,6-collidine to inactivate surface acid sites on the HZSM-23. The HZSM-23 had a silica to alumina ratio of approximately 110 and an alpha value of about 25. Reaction temperature was fixed at 225° C., and the total reaction time was 10 hours in each case. Results and certain reaction conditions are summarized in Table 10.

TABLE 10
EFFECT OF REACTION PRESSURE ON BRANCHING

| | | | | |
|---|---|---|---|---|
| $C_3=$ Press, psig | 250 | 750 | 1250 | 250 |
| He Press, psig | 0 | 0 | 0 | 1000 |
| Gms Catalyst | 7.7 | 7.7 | 7.7 | 7.7 |
| Temp, C. | 225 | 225 | 225 | 225 |
| Gms Liq Prod | 12.7 | 50.1 | 44.8 | 14.2 |
| Carbon Skeleton | | | | |
| C9 | | | | |
| >Di-Methyl | 28.1 | 10.9 | 8.0 | 40.8 |
| Mono-Methyl | 65.5 | 74.8 | 58.6 | 50.6 |
| Normal | 6.4 | 14.3 | 33.3 | 8.6 |
| Me/C9 | 1.36 | 1.02 | 0.79 | 1.53 |
| C12 | | | | |
| >Di-Methyl | 40.1 | 12.7 | 9.8 | 47.4 |
| Mono-Methyl | 55.6 | 76.1 | 59.2 | 48.7 |
| Normal | 4.2 | 11.2 | 30.9 | 3.9 |
| Me/C12 | 1.56 | 1.08 | 0.84 | 1.67 |
| C15 | | | | |
| >Di-Methyl | 47.3 | 15.4 | 10.6 | 47.3 |
| Mono-Methyl | 49.5 | 75.6 | 66.1 | 48.4 |
| Normal | 3.3 | 9.0 | 23.3 | 4.3 |
| Me/C15 | 1.68 | 1.14 | 0.93 | 1.67 |

The two reaction conditions giving higher $C_{12+}$ selectivity (250 psig propylene) gave the most highly branched oligomers. All results to date suggest that regardless of how selectivity to higher oligomers is achieved, it is at the expense of product linearity.

EXAMPLE XII

A run of extended duration was carried out in a stirred one-gallon autoclave. In accordance with this run, sufficient propylene was charged to the reactor to give the desired reaction pressure at temperature. Propylene was fed on demand during the reaction to maintain this pressure. When enough liquid product had been made to fill the autoclave to approximately one-half of capacity, the product was discharged through a dip tube. Additional propylene was then charged to give the desired pressure and the reaction resumed. This run lasted for slightly longer than two months. No amine (i.e. 2,4,6-collidine) was used as a cofeed during the entire duration of this run.

In this run, 125 gms. HZSM-23/alumina extrudate were treated with 1.5 gms. 2,4,6-collidine and the catalyst charged to the autoclave. The HZSM-23 had a silica to alumina ratio of approximately 110 and an alpha value of about 25. This run continued for a total of 81 days producing approximately 85 kg crude propylene oligomer. The temperature of the reaction was constantly maintained at 225° C. and the pressure of the autoclave during the reactions was constantly maintained at 750 psig. The selectivity to $C_{12+}$ product varied essentially randomly between about 30 and 40 wt.% of the total product. A plot of this $C_{12+}$ product selectivity indicated that the average selectivity to $C_{12+}$ product was essentially constant over the 81 day duration of the run. The average number of methyl side groups in the $C_{12}$ product increased very gradually from slightly less than about 1.20 to about 1.35 over the duration of the run. Consistent with data discussed hereinabove, the highest level of methyl branching per $C_{12}$ molecule (e.g., 1.35–1.40) was observed on the three days when the $C_{12+}$ product selectivity was also observed to be relatively high (e.g., at about 40 wt.%).

EXAMPLE XIII

This Example provides data regarding the use of a propane diluent along with a propylene feed. An HZSM-23 extrudate (65% zeolite, 35% alumina binder) was treated with a solution of 2,4,6-collidine in pentane, and the pentane was permitted to evaporate at room temperature. This HZSM-23 had a silica to alumina ratio of approximately 110 and an alpha value of about 25. This catalyst was charged to a fixed bed tubular reactor. In Runs 13-A and 13-B a synthetic propane/propylene (P/P) feed (60% propylene/40% propane) was fed into the reactor. In Run 13-C propylene in the absence of a propane diluent was fed into the reactor. 2,4,6-Collidine (i.e., "Poison") was also fed into the reactor in varying amounts. Consistent with previous observations, propylene partial pressure was the major factor in determining both carbon number distribution and branching. Product distributions and branching observed at two reaction pressures with the synthetic P/P mix and with pure propylene feed are shown in Table 11.

TABLE 11
COMPARISON OF PROPANE/PROPYLENE VS PURE PROPYLENE FEEDS

| Run Number | 13-A | 13-B | 13-C |
|---|---|---|---|
| Feed | P/P | P/P | $C_3=$ |
| Temp (setting) | 185 | 185 | 185 |
| Temp (hot spot) | 212 | 217 | 214 |
| Pressure, psig | 500 | 800 | 500 |
| $C_3=$ WHSV, hr$^{-1}$ | 0.21 | 0.19 | 0.24 |
| $C_3$ WHSV, hr$^{-1}$ | 0.15 | 0.13 | 0.00 |
| Poison, ppm | 92 | 83 | 200 |
| $C_3=$ Conv, wt. % | 74.6 | 74.3 | 91.1 |
| Prod Dist, wt. % | | | |
| $C_6$ | 40.8 | 51.4 | 58.7 |
| $C_9$ | 24.4 | 23.5 | 20.1 |
| $C_{12}$ | 13.6 | 11.9 | 11.0 |
| $C_{15}$ | 11.8 | 7.8 | 6.4 |
| $C_{18}$ | 5.7 | 3.2 | 2.4 |
| $C_{21}+$ | 3.8 | 2.1 | 1.4 |
| $C_{12}+$ Select | 34.9 | 25.0 | 21.2 |
| Branching | | | |
| Me/$C_9$ | 1.36 | 1.08 | 1.05 |
| Me/$C_{12}$ | 1.68 | 1.27 | 1.19 |
| Me/$C_{15}$ | 1.85 | 1.39 | 1.28 |

These data illustrate the effect of propylene partial pressure. Runs 13-A and 13-C are at the same total reactor pressure (500 psig) while Runs 13-B and 13-C are at essentially the same propylene partial pressure. The slightly higher linearity and lower $C_{12+}$ selectivity observed with pure propylene at 500 psig versus P/P mix at 800 psig (480 psig $C_3=$) may be due in part to the higher poison level in the former run. It can be seen that the two runs at the same propylene partial pressure give very similar product distributions and branching. This suggests that as diluent is added, the reaction should be run at a higher pressure in order to obtain the same product quality.

EXAMPLE XIV

This Example provides data regarding the use of a 1-butene feedstock. 15.4 gms HZSM-23 extrudate (65% zeolite, 35% alumina binder) were treated with 0.088 grams 2,4,6-collidine in approximately 50 cc pentane. This HZSM-23 had a silica to alumina ratio of approximately 110 and an alpha value of about 25. The pentane was allowed to evaporate, at room temperature, and the surface modified catalyst was charged to a fixed bed tubular reactor. 1-butene was metered to the reactor, and a solution of 2,4,6-collidine (i.e., "Poison") in pentane was also metered to the reactor at 200 ppm of 2,4,6-collidine per weight of total feed into the reactor. Results are summarized in Tables 12 and 13.

TABLE 12

PRODUCT DISTRIBUTIONS OBSERVED WITH 1-BUTENE

| Run Number | 14-A | 14-B | 14-C | 14-D |
|---|---|---|---|---|
| REACTION COND | | | | |
| Temp (setting) | 180 | 185 | 195 | 205 |
| Temp (hot spot) | 217 | 224 | 236 | 249 |
| Pressure, psig | 540 | 530 | 530 | 520 |
| $C_4$ = WHSV, | 0.29 | 0.27 | 0.22 | 0.21 |
| Poison, ppm | 200 | 200 | 200 | 200 |
| Prod Dist | | | | |
| $C_8$ | 38.4 | 36.5 | 33.4 | 26.2 |
| $C_{12}$ | 33.1 | 34.8 | 38.5 | 43.0 |
| $C_{16}$ | 12.4 | 14.3 | 15.4 | 21.9 |
| $C_{20}$ | 4.5 | 5.1 | 3.5 | 7.0 |
| $C_{24}$ | 1.5 | 1.8 | 1.6 | 2.2 |
| $C_{28}^+$ | 1.2 | 1.4 | 0.4 | 1.4 |
| $C_{12}^+$ Select | 52.7 | 57.3 | 59.4 | 75.6 |
| $C_{16}^+$ Select | 19.6 | 22.5 | 21.0 | 32.5 |
| $C_4$ = Conv | 28.5 | 44.3 | 69.3 | 95.4 |

TABLE 13

CARBON SKELETON DISTRIBUTIONS OBSERVED WITH 1-BUTENE

| RUN NUMBER | 14-A | 14-B | 14-C | 14-D |
|---|---|---|---|---|
| REACT COND | | | | |
| TEMP (SETTING) | 180 | 185 | 195 | 205 |
| TEMP (HOT SPOT) | 217 | 224 | 236 | 249 |
| PRESSURE | 540 | 530 | 530 | 520 |
| $C_4$ = WHSV | 0.29 | 0.27 | 0.22 | 0.21 |
| POISON, PPM | 200 | 200 | 200 | 200 |
| CARBON SKELETON | | | | |
| $C_8$ | | | | |
| DI-ME(a) | 6.7 | 8.6 | 11.5 | 20.1 |
| MONO-ME | 79.3 | 79.3 | 77.9 | 72.3 |
| NORMAL | 14.1 | 12.1 | 10.6 | 7.6 |
| ME/$C_8$(b) | 0.96 | 1.01 | 1.07 | 1.23 |
| $C_{12}$ | | | | |
| DI-ME | 13.8 | 16.1 | 19.2 | 23.2 |
| MONO-ME | 78.2 | 76.7 | 74.0 | 71.1 |
| NORMAL | 8.0 | 7.3 | 6.8 | 5.7 |
| ME/$C_{12}$ | 1.13 | 1.17 | 1.22 | 1.29 |
| $C_{16}$ | | | | |
| DI-ME | 23.0 | 24.5 | 24.2 | 26.2 |
| MONO-ME | 71.5 | 70.1 | 68.4 | 68.7 |
| NORMAL | 5.5 | 5.5 | 7.4 | 5.1 |
| ME/$C_{16}$ | 1.29 | 1.31 | 1.29 | 1.34 |

(a) All values for isomer distributions are normalized percentages for that carbon number.
(b) Values for number of methyl branches were calculated assuming an average of 2.5 for di-methyl component. As compared with the use of a propylene feed, much higher $C_{12+}$ selectivities were realized, but most of the $C_{12+}$ oligomers were actually $C_{12}$. There was a much more dramatic fall-off with carbon number beyond $C_{12}$ observed for 1-butene oligomerization than was observed with propylene. The isomer distributions observed for a $C_{12}$ produced from 1-butene were essentially identical to those observed to be produced by propylene oligomerization.

EXAMPLE XV

This Example regards the effect of a certain steam treatment on the catalyst performance of two different samples of ZSM-23, prepared by different synthesis techniques. One of these catalysts is designated herein as Catalyst A and the other of these catalysts is designated as Catalyst C. Each of these unsteamed Catalysts A and C were HZSM-23 extrudates (65% zeolite, 35% alumina binder). This HZSM-23 had a silica to alumina ratio of approximately 110 and an alpha value of about 25. Samples of each of these unsteamed catalysts A and C were steamed for four hours at 950° F. in 100% steam. Catalyst B is designated herein as the steamed counterpart of Catalyst A, and Catalyst D is designated herein as the steamed counterpart of Catalyst C.

7.7 grams of each of Catalysts A, B, C and D were treated with 0.044 grams of a solution of 2,4,6-collidine in pentane, and the pentane was permitted to evaporate at room temperature. Each of Catalysts A, B, C and D were charged to a 450 cc stirred autoclave along with approximately 75 cc propylene, and the reactor was heated to 225° C. At reaction temperature, additional propylene was added, if necessary, to give a total reaction pressure of 750 psig. Propylene was then added upon demand to maintain 750 psig. Initially, all runs were to be for a total of 10 hours reaction time. However, the greater activity for the steamed catalysts necessitated termination of these reactions at short times. Results of these four runs are given in Table 14. This data indicates that this particular steam treatment resulted in a catalyst that is 3–4 times more active for propylene conversion relative to that observed for the unsteamed parent. In addition to reacting propylene at a faster rate, the steamed catalysts are also more selective for formation of the higher oligomers. Branching is slightly higher with the steamed catalysts.

TABLE 14

EFFECT OF STEAMING ON ZSM-23 PERFORMANCE

| Catalyst | A | B | C | D |
|---|---|---|---|---|
| Run Time, hrs | 10 | 5 | 10 | 3 |
| Gms liquid product | 50.1 | 102.8 | 81.3 | 64.8 |
| Rate, gms/hr | 5.0 | 20.6 | 8.1 | 21.6 |
| Prod Dist. wt. % | | | | |
| $C_6$ | 62.3 | 49.6 | 57.3 | 52.5 |
| $C_9$ | 20.6 | 23.0 | 24.4 | 21.8 |
| $C_{12}$ | 9.8 | 12.3 | 8.7 | 10.9 |
| $C_{15}$ | 4.7 | 8.5 | 5.9 | 8.0 |
| $C_{18}$ | 1.7 | 3.8 | 2.4 | 4.0 |
| $C_{21}^+$ | 0.9 | 2.7 | 1.3 | 2.9 |
| $C_{12}^+$ Select | 17.1 | 27.3 | 18.3 | 25.8 |
| $C_{15}^+$ Select | 7.3 | 15.0 | 9.6 | 14.9 |
| Branching | | | | |
| Me/$C_9$ | 1.02 | 1.14 | 1.31 | 1.28 |
| Me/$C_{12}$ | 1.08 | 1.28 | 1.27 | 1.35 |
| Me/$C_{15}$ | 1.14 | 1.28 | 1.23 | 1.34 |

Catalyst A: unsteamed
Catalyst B: steamed A
Catalyst C: unsteamed
Catalyst D: steamed C

EXAMPLE XVI

The preparation of a dealuminized mordenite catalyst, which was used in Example XVII set forth hereinafter, is described in this Example. A ten gram sample of a mordenite catalyst (Zeolon 100) was heated from 50° to 400° C. over 4 hrs. It was kept at this temperature for 1.5 hrs., then raised to 670° C. over 2 hrs. where it was kept for 2 hrs. The resulting 8.5 g catalyst was stirred for 2 hrs. in 170 ml of 0.5N HCl, then refluxed overnight. This acid refluxed catalyst was filtered and added to 170 ml distilled water. After refluxing overnight, the catalyst was filtered and washed with about 1500 ml distilled water. It was calculated for several hours at 568° C. before use.

EXAMPLE XVII

In accordance with this Example, benzene was alkylated with an olefin mixture over the dealuminized mordenite prepared in Example XVI. The olefin mixture was propylene tetramer (1.3 methyl branches per chain) prepared by oligomerizing propylene over a ZSM-23 catalyst having surface acid sites inactivated with 2,4,6-collidine and separating out the $C_{12}$ fraction. This olefin mixture was percolated through activated alumina prior to use. To an oven-dried flask under N$_2$ was added 10 ml perked C$_{12}$ olefin (0.05 mol), 50 ml benzene (0.56 mol) and 0.6 g dealuminized mordenite. After 6 hrs., GC showed about 10% reaction. Another 0.5 g catalyst was added and the mixture was refluxed 64 hrs. GC showed about 90% reaction. Another 0.25 g catalyst was added and the mixture was refluxed an additional 24 hr. The reaction was cooled, filtered, and evaporated to 10.15 g product, which still contained 4% unreacted olefin. All of the dodecylbenzenes were fractionally distilled with the desired product distilling at 68°–111° C. (mostly 90°–94° C.), 0.3–0.4 mmHg.

EXAMPLE XVIII

In accordance with this Example, dodecylbenzene, prepared in accordance with Example XVII, was sulfonated. A 3-neck round-bottomed flask, equipped with a thermometer, and dropping funnel was charged with 5 g dodecylbenzene (0.021 mol) prepared in accordance with Example XVII. To these contents were added dropwise over 35 minutes 3.0 ml 30% fuming H$_2$SO$_4$ (0.022 mol SO$_3$), keeping the temperature below 30° C. with an ice bath. The dark brown mixture was then heated to 60° C. for one hour. Upon cooling, the mixture was pipetted into 40 ml 10% NaOH (aq) with vigorous stirring, causing a large amount of tan precipitate to form. The mixture was made basic and filtered through an F frit. The resulting pasty solid was added to benzene, and the benzene and remaining water were evaporated. The tan solid was dried in a vacuum oven at 110° C., yielding 7.2 g. This product was added to about 700 ml absolute ethanol. After stirring and heating, the insoluble sodium sulfate was filtered off and the ethanol was evaporated yielding 4.0 g alkylbenzene sulfonate. Liquid chromatography showed this product to contain less than 10% sodium sulfate. This material was submitted for biodegradation testing without further purification and was found to be biodegradable.

More particularly, this alkylbenzene sulfonate made with the present oligomers (nearly linear) was as biodegradable as an alkylbenzene sulfonate prepared from 1-dodecene (linear) and using AlCl$_3$ as the alkylation catalyst. In this test microbial cultures were acclimated to surfactants at least three weeks prior to tests. The EPA Shake Flask Method was used. This method is described at Federal Register V. 44(53), A-5.1, Mar. 16, 1979, pp. 16274–16275. Results are summarized in Table 15.

TABLE 15
ALKYLBENZENE SULFONATE ULTIMATE BIODEGRADABILITY

| C$_{12}$ Olefin structure | Alkylation Catalyst | % of Test Compound Converted to CO$_2$ (8 days) |
|---|---|---|
| Linear | AlCl$_3$ | 27 |
| Nearly Linear | Dealuminized Mordenite | 25 |

We claim:

1. A surface-inactivated catalyst composition comprising acid crystalline ZSM-23 having active internal Brösted acid sites and containing a surface-inactivating amount of 2,4,6-collidine.

2. The catalyst composition of claim 1 wherein said ZSM-23 is an aluminosilicate having a silica-to-alumina mole ratio of at least 12.

3. The catalyst composition of claim 2 wherein the ZSM-23 has an acid cracking value of at least about 10.

4. A method of making a shape-selective catalyst comprising
    contacting acid medium pore ZSM-23 zeolite with a solution of a 2,4,6-collidine deactivating agent to chemisorb said agent onto the zeolite surface for rendering said zeolite surface substantially inactive for acidic reaction.

* * * * *